United States Patent [19]

Hercelin et al.

[11] 4,107,333

[45] Aug. 15, 1978

[54] SKIN CARE WITH A COSMETIC COMPOSITION CONTAINING OLEYL ACETATE

[75] Inventors: Bernard Hercelin, Clermont; Jean-François Hamon, Saint-Quen l'Aumone, both of France

[73] Assignee: Laboratories Cassenne, Paris, France

[21] Appl. No.: 669,026

[22] Filed: Mar. 22, 1976

[30] Foreign Application Priority Data

Mar. 26, 1975 [FR] France .................................. 75 09438

[51] Int. Cl.² ............................................. A61K 7/48
[52] U.S. Cl. ........................................ 424/365; 424/47; 424/311; 560/261
[58] Field of Search ........................... 424/311, 365, 47

[56] References Cited

U.S. PATENT DOCUMENTS

| 3,052,607 | 9/1962 | Hirsh | 424/365 |
| 3,098,795 | 7/1963 | Kreps | 424/365 |
| 3,624,221 | 11/1971 | Lange | 424/365 |

FOREIGN PATENT DOCUMENTS 2,243,281  3/1974  Fed. Rep. of Germany ........... 424/365

*Primary Examiner*—Albert T. Meyers
*Assistant Examiner*—Vera C. Clarke
*Attorney, Agent, or Firm*—Bacon & Thomas

[57] ABSTRACT

A process of skin care characterized by applying thereto a cosmetic composition containing oleyl acetate.

3 Claims, No Drawings

SKIN CARE WITH A COSMETIC COMPOSITION CONTAINING OLEYL ACETATE

It is well known that the surface of the skin is covered with bacteria. These bacteria, and notablly the strain *Corynebacterium acnes* secrete lipases which act on the sebum and the triglycerides present on the skin to produce fatty acids. These fatty acids cause a certain number of unaesthetic skin reactions such as redness, which may be due to inflammations, eruptions of the skin, and the like which are generally localized on the face, upper chest and back.

It has now been discovered that oleyl acetate, the preparation of which is described in 1924 (Helferich, Schafer, B 57 p 1914), possesses the ability to inhibit the effect of lipase secreted by the *Corynebacterium acnes.*

The substance which exerts an active inhibition on the lipases secreted by the *Corynebacterium acnes* may advantageously be incorporated in a cosmetic composition to maintain the health of the skin and avoid the above-mentioned unaesthetic reactions.

The present invention has as one of its objects a new cosmetic composition characterized in that it contains an effective amount of oleyl acetate. The other constituents of the composition may be any suitable base which is conveniently used for the preparation of cosmetic skin applications. In accordance with this invention, the cosmetic composition which may be used is characterized by the fact that it contains an effective amount and preferably from 0.1 to 50 weight percent oleyl acetate. More preferably, the composition contains from 3 to 30 percent oleyl acetate.

The compositions of the present invention may advantageously be applied locally for treatment and care of the skin because of the important anti-lipases property of the compositions as illustrated in the examples contained in this application. The compositions may be applied at any time but generally applications can be made, for example, in the morning and in the evening.

The compositions of the present invention may be in any suitable form for application and may be solid, liquid or gaseous and may be in a form currently utilized in conventional cosmetic applications using carriers such as, for example ointments, creams, gels, salves, lotions, milks, bath oils, masks or aerosols. Among the preferred forms of the compositions of this invention are those compositions which are present in the form of an ointment, cream, gel, lotion, bath oil or aerosol.

The invention also has as another object a process of skin care characterized in that a composition as previously defined containing an effective amount of oleyl acetate is applied to the skin.

The cosmetic compositions of the present invention can be prepared according to conventional methods. The oleyl acetate may be incorporated in conventional bases utilized to form cosmetic compositions, such as polyethylene glycols, waxes, fatty substances including fats, soaps, fatty acids, lecithin, stearic acid derivatives, alcohols, such as stearyl alcohol, ketostearyl alcohol, vegetable oils, such as sweet almond oil, castor oil, mineral oils and the like. Other materials such as wetting agents, thickeners, preservers, stabilizers, perfumes, coloring agents and other substances conventionally used in the preparation of cosmetic materials may also be added to the composition when desired. Specific examples of these compositions are given in the examples which follow.

Oleyl acetate which is contained in the cosmetic compositions of the present invention may be prepared as follows: To a reactor provided with a water trap, 804 grams of oleyl alcohol, 270 grams of acetic acid, 500 ml of benzene and 8 grams of paratoluene sulfonic acid are successively added. The reaction mixture is brought to reflux and maintained at reflux for 6 hours. Then, about 70 ml of water is separated; benzene and the excess acetic acid are evaporated under vacuum. The residue was dissolved in 1 liter of ether, washed with water and with a saturated sodium bicarbonate solution and finally again with water; then dried over magnesium sulfate and treated with activated carbon and distilled under vacuum. 720 grams of oleyl acetate in the form of an almost colorless oil having a boiling point of 180° C (1.5 mm/mercury) was obtained.

The following are non-limiting working examples of compositions of the present invention:

EXAMPLE 1

An ointment for skin-care is prepared by simple mixing of the following ingredients:

| | |
|---|---|
| oleyl acetate | 5 grams |
| ketostearyl alcohol | 30 grams |
| high viscosity paraffin oil | 35 grams |
| white vaseline Codex q.s.p. | 100 grams |

EXAMPLE 2

An ointment for skin care is prepared by simple mixing of the following ingredients:

| | |
|---|---|
| oleyl acetate | 20 grams |
| ketostearyl alcohol | 30 grams |
| high viscosity paraffin oil | 35 grams |
| white vaseline Codex q.s.p. | 100 grams |

EXAMPLE 3

An ointment for the skin-care is prepared by simple mixing of the following ingredients:

| | |
|---|---|
| oleyl acetate | 10 grams |
| glycerin monostearate | 11 grams |
| polyglycolic ether of saturated fatty alcohol | 3 grams |
| di-tertiobutylhydroxy toluene | 0.3 grams |
| triglycerides of saturated fatty alcohols containing 16-18 carbon atoms q.s.p. | 100 grams |

EXAMPLE 4

A cream for the skin-care is prepared having the following formulations:

| | |
|---|---|
| oleyl acetate | 3 grams |
| ketostearly alcohol | 9 grams |
| ketostearyl alcohol sodium sulfate | 12 grams |
| 2-octyl dodecanol | 15 grams |
| sweet almond oil | 6 grams |
| water q.s.p. | 100 grams |

The oleyl acetate, ketostearyl, alcohol, ketostearyl alcohol sodium sulfate, 2-octyl dodecanol and the oil of sweet almond are successively added and mixed. The mixture then obtained is heated to about 70° C and this fatty mixture is poured into water which has been previously heated to 70° C. The mixture is agitated vigorously until an emulsion is obtained.

EXAMPLE 5

A gel for the care of the skin is prepared according to the following formula:

| | |
|---|---|
| oleyl acetate | 2 grams |
| ethyl alcohol 96° | 40 grams |
| polyglycolic ether of saturated fatty alcohols | 3 grams |
| Carbopol 940 (carboxyvinylpolymer) | 3 grams |
| triethanolamine | 2.5 grams |
| water q.s.p. | 100 grams |

The Carbopol 940 is mixed with water followed by the addition of triethanolamine then under agitation the oleyl acetate, the ethyl alcohol, and the polyglycolic ether of saturated fatty alcohols are added. The mixing is continued until a homogeneous gel is obtained.

EXAMPLE 6

Lotion for the skin-care. A lotion is prepared by mixing the following ingredients:

| | |
|---|---|
| oleyl acetate | 20 grams |
| ethanol | 60 grams |
| Carbopol 940 (carboxyvinylpolymer) | 0.3 grams |
| monoethanolamine | 0.25 grams |
| sorbitan tri-oleate | 3 grams |
| water q.s.p. | 100 grams |

EXAMPLE 7

Bath oil for the skin-care. A bath oil in accordance with the present invention is prepared by simple mixing of the following ingredients:

| | |
|---|---|
| oleyl acetate | 30 grams |
| glycerol mono-oleate | 35 grams |
| 1,2-propylene glycol | 5 grams |
| 2-octyldodecanol | 30 grams |

EXAMPLE 8

Aerosol for the skin-care. An aerosol is prepared having the following composition:

| | |
|---|---|
| oleyl acetate | 20 grams |
| trichloromonofluoromethane q.s.p. | 100 grams |

STUDY OF THE ANTI-LIPASE ACTIVITY (IN VITRO)

An emulsion which contains 10 ml of substrate (olive oil) and a lipase extract consisting of 1 ml of a solution of 30 mg/ml of a supernatant lipase fraction which was obtained by salting out a culture of *Corynebacterium Acnes* (ATCC 11 828) with 2.4 molar ammonium sulfate (pH 6.5) was incubated at 37° C (pH 9.00 to 7.50).

The kinetics of the enzymatic activity (milli-moles fatty acid liberated) was registered by pH determination.

The initial average lipase activity ($\overline{ALo}$) was obtained by the average slope of the curve obtained from a plot of the milli-moles of fatty acid liberated as a function of time, i.e. (milli-moles fatty acid liberated) = f (time), during the course of the first 3 minutes which follow the return to the initial pH. The average was determined on the basis of several tests.

The same operation is repeated under identical conditions several times in the presence of X mg of the product which inhibits lipase produced from Corynebaceterium acnes. A new lipase actvity is obtained, $\overline{AL}$.

The difference $\overline{ALo} - \overline{AL}$ reported per gram of product gives the average inhibitory activity of the tested product in Units Enzymatic Inhibition per gram (U.E.I./g).

Under these conditions, oleyl acetate has an average inhibition of 1.12 U.E.I./g. which indicates that oleyl acetate has an important antilapase activity.

What is claimed is:

1. A process for the care of the skin which comprises applying a cosmetic composition for skin care containing an effective amount of oleyl acetate and a carrier to the skin in an amount effective care of the skin.

2. The process of claim 1 wherein the effective amount of oleyl acetate is from 0.1 to 50 percent.

3. A process of claim 2 wherein the oleyl acetate is present in an amount of from 3 to 30 percent.

* * * * *